June 15, 1976
J. C. MIKKELSEN
POINSETTIA PLANT
Filed May 7, 1975
Plant Pat. 3,912
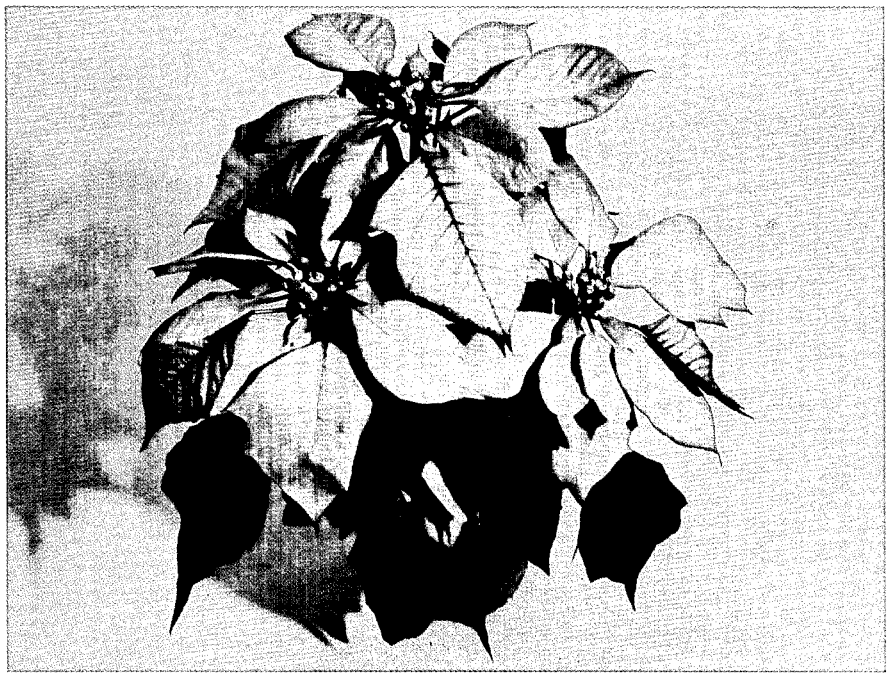

United States Patent

Plant Pat. 3,912

Patented June 15, 1976

3,912

POINSETTIA PLANT

James C. Mikkelsen, Ashtabula, Ohio, assignor to Mikkelsens Inc., Ashtabula, Ohio Filed May 7, 1975, Ser. No. 575,435

Int. Cl. A01h *5/00*

U.S. Cl. Plt.—86 1 Claim

The present invention relates to a new and distinctive cultivar of poinsettia plant known by the varietal name Triumph, and botanically known as *Euphorbia pulcherrima.*

The new cultivar is a mutation of an unpatented variety which has been in my possession for several years and which is known in the floriculture industry as MIKKEL Rochford.

The new cultivar has been asexually reproduced by cuttings in the greenhouses of Mikkelsens Inc., Ashtabula, Ohio for a period of 18 months, and has been found to retain its distinctive characteristics through successive propagations.

The following characteristics distinguish the new cultivar from its parent and from other poinsettias commercially known and used in the floriculture industry:

(1) The new cultivar will develop flowering parts and red bracts at 52°–54° F. night temperatures which is well below the recommended night temperatures of 60°–65° F. for most poinsettia cultivars being grown at this time. This allows for considerable savings of energy during the normal cropping period.

(2) The ability to produce heavy rigid stems with close internodes and comparatively small foliage at 52°–54° eliminates the use of growth regulators during the forcing period if low temperatures can be maintained.

(3) The small foliage, close internodes, and upright stems of the new cultivar allows the grower to produce more top quality plants per square foot than with other presently available cultivars.

(4) The ability to produce a branching poinsettia plant with upwards of four to eight vigorous shoots after the removal of the apical tip prior to the critical daylength date.

(5) The bracts have a durable quality that reduces the damage often associated with other poinsettias during handling, packaging, and transporting.

(6) In comparison to many other poinsettias that have been tested with low temperatures and which subsequently drop their foliage when brought into warmer environments, this new cultivar does not drop its foliage for a considerable length of time.

(7) At low temperatures the bracts of this new cultivar are quite resistant to botrytis infection, whereas many of the present cultivars are readily infected.

(8) Leaf petiole is quite distinct, being dark red.

The accompanying colored photographic drawing illustrates the overall appearance of the new cultivar, with the colors being as true as possible to obtain in color reproductions of this type.

The following is a detailed description of the new cultivar based on plants produced under commercial practices in the greenhouse of Mikkelsens Inc., Ashtabula, Ohio.

Color references are to the Royal Horticultural Society Colour Chart except where general color terms of ordinary dictionary significance are used.

Parentage: Mutation of the cultivar MIKKEL Rochford.

Form of plant: Upright and normally not self-branching. When the apical tip is removed under favorable growing conditions, four to eight nodal shoots will develop.

Growth habit: At normal poinsettia growing environments of 65° night temperature the overall growth of the new cultivar is 20% shorter than the Paul Mikkelsen poinsettia (U.S. Plant Pat. No. 2,328). When this cultivar is grown at 52°–54° F. night temperature it will be more vigorous than Paul Mikkelsen and will flower whereas Paul Mikkelsen will not flower at such low temperatures.

Rooting: Rooting is approximately 20% slower than Paul Mikkelsen relative to the time of year.

Blooming season: When grown at 65° F. night temperature and 68°–72° days the new cultivar will flower in approximately 65 to 70 days. When grown at 52°–54° nights and 65° to 68° day temperatures it will flower in approximately 75–80 days.

Blooming habit: Typical of poinsettias, having a central terminal cyathia with three subsequent flowering stems developing below it.

Foliage:

*Size.*—At 65° F. average for poinsettias. At 52°–54° F. foliage is considered small, approximately 8 cm. wide by 11 cm. long not including the petiole.

Quantity: Average for poinsettias.

Color:

*New foliage.*—Upper side—darker than yellow green 145A; under side—near yellow green 145A.

*Old foliage.*—Upper side—green 137A to 147A; under side—green 146 B–C.

*Leaf petiole.*—Dark red 59A.

Shape: Oak leaf pattern similar in shape to the Paul Mikkelsen poinsettia.

Texture:

*Upper side.*—Smooth, veins recessed—typical.

*Under side.*—Coarse veins protruding—typical.

Edge of margin: From near complete in lower leaves to sharp sinuses in upper leaves below the bracts.

Aspect: Nearly right angles to the stem.

Disease resistance: Quite resistant to botrytis on the bracts. No particular root or stem rot problems have been seen to date.

Flowers (cyathia):

*Borne.*—In tight clusters initially, later separating into three lateral strings as the peduncles elongate.

*Quantity.*—Average.

*Continuity.*—During the normal flowering season the cyathias continue to initiate and develop for three to four months.

*Bracts.*—The initial bracts that develop from the last true leaves just beneath the primary cyathia have an oak leaf pattern; the bracts developing with succeeding cyathias become more oblate, these quite narrow and shorter so that the total bract head becomes quite full and compact with smooth surfaced multiformed red bracts.

*Color.*—Young bracts, red 45c to 46c with orange lustre. Mature bracts, darker red than 45A but not as dark as 46A. Underside of bracts 46D and 47C.

*Reproductive organs.*—Immature cyathias 5 to 6 mm. in diameter.

*Stamens.*—Color, red 53A.

*Pollen.*—Color, Yellow 16A.

*Styles.*—Color, red 46A.

*Ovaries.*—Color, externally-green.

I claim:

1. A new and distinct cultivar of poinsettia plant characterized particularly as to novelty by the combined characteristics of development of flowers and red bracts at 52°–54° F.; heavy, rigid upright stems; small foliage and close internodes; four to eight vigorous shoots after removal of the apical tip; durable bracts; long lasting foliage; resistance to botrytis infection, and by its distinct, dark red leaf petiole.

No references cited.

ROBERT E. BAGWILL, Primary Examiner